US012781255B2

(12) United States Patent
Kuwahara

(10) Patent No.: US 12,781,255 B2
(45) Date of Patent: Nov. 3, 2026

(54) MICROBE THAT PRODUCES CAROTENOID

(71) Applicant: ENEOS MATERIALS CORPORATION, Tokyo (JP)

(72) Inventor: Daichi Kuwahara, Tokyo (JP)

(73) Assignee: ENEOS MATERIALS CORPORATION, Tokyo (JP)

( * ) Notice: Subject to any disclaimer, the term of this patent is extended or adjusted under 35 U.S.C. 154(b) by 406 days.

(21) Appl. No.: 18/285,969

(22) PCT Filed: Mar. 18, 2022

(86) PCT No.: PCT/JP2022/012581
§ 371 (c)(1),
(2) Date: Oct. 6, 2023

(87) PCT Pub. No.: WO2022/220014
PCT Pub. Date: Oct. 20, 2022

(65) Prior Publication Data

US 2024/0182943 A1 Jun. 6, 2024

(30) Foreign Application Priority Data

Apr. 13, 2021 (JP) ................................ 2021-067540
Sep. 30, 2021 (JP) ................................ 2021-160741

(51) Int. Cl.
*C12P 23/00* (2006.01)
*C12N 9/02* (2006.01)

(52) U.S. Cl.
CPC ............ *C12P 23/00* (2013.01); *C12N 9/0083* (2013.01)

(58) Field of Classification Search
CPC ....... C12P 23/00; C12N 9/0083; C12N 1/205; C12N 15/102; C12N 1/20; C12N 15/01; C12R 2001/01; C12Y 114/99; Y02P 60/87
See application file for complete search history.

(56) References Cited

U.S. PATENT DOCUMENTS

2007/0105189 A1 5/2007 Tsubokura et al.
2013/0030218 A1 1/2013 Hirasawa et al.

FOREIGN PATENT DOCUMENTS

JP 2005-87097 A 4/2005
KR 10-2006-0060039 A 6/2006
KR 10-2013-0040823 A 4/2013
WO 2011/122616 A1 10/2011

OTHER PUBLICATIONS

Teruhiko Ide, Megumi Hoya, Toru Tanaka, Shigeaki Harayama, Enhanced production of astaxanthin in *Paracoccus* sp. strain N-81106 by using random mutagenesis and genetic engineering, Biochemical Engineering Journal, vol. 65, 2012, pp. 37-43. doi.org/10.1016/j.bej.2012.03.015 (Year: 2012).*

WO-2011122616-A1, English translation, 2011, 18 pages of PDF. (Year: 2011).*

Tsushima et al., "Inhibitory Effect of Natural Carotenoids on Epstein-Barr Virus Activation Activity of a Tumor Promoter in Raji Cells. A Screening Study for Anti-tumor Promoters," *Biol. Pharm. Bull.*, 1995, vol. 18, No. 2, pp. 227-233.

Yamaguchi et al., "Osteoporosis Prevention by Beta-Cryptoxanthin," *ACS Symp Ser* (*Am Chem Soc*), 2008, No. 993, pp. 408-418.

Lee et al., "Cloning and characterization of the astaxanthin biosynthesis gene cluster from the marine bacterium *Paracoccus haeundaensis*," *Gene*, Jan. 23, 2006, vol. 370, pp. 86-95.

Ye et al., "Mutational and functional analysis of the beta-carotene ketolase involved in the production of canthaxanthin and astaxanthin," *Applied and Environmental Microbiology*, 2006, vol. 72, No. 9, pp. 5829-5837.

Henke et al., "Production of the Marine Carotenoid Astaxanthin by Metabolically Engineered *Corynebacterium glutamicum*," *Marine Drugs*, Jun. 30, 2016, vol. 14, No. 7, article No. 124, pp. 1-21.

Ukibe et al., "Metabolic engineering of *Saccharomyces cerevisiae* for astaxanthin production and oxidative stress tolerance," *Applied and Environmental Microbiology*, Oct. 2, 2009, vol. 75, No. 22, pp. 7205-7211.

International Search Report Issued in PCT/JP2022/012581, dated May 17, 2022, with English translation thereof.

Written Opinion of the International Searching Authority for No. PCT/JP2022/012581, dated May 17, 2022, with English translation thereof.

Ishibashi, T., "Current status and prospects of carotenoid research and development of commercial production of carotenoids using *Paracoccus* sp.," *Seibutsu Kogaku Kaishi* (*Journal of the Society for Bioscience and Bioengineering, Japan*), vol. 93, No. 7, Jul. 25, 2015, pp. 388-390, XP093310111, JP ISSN: 0919-3758. Retrieved from the Internet: https://www.sbj.or.jp/wp-content/uploads/file/sbj/9307/9307_tokushu_2.pdf, with English machine translation thereof.

Extended European Search Report issued Sep. 25, 2025 in European patent application No. 22787940.0, with English machine translation thereof.

Office Action issued Feb. 10, 2026 in Japanese patent application No. 2023-514537, with English machine translation thereof.

Office Action issued Feb. 19, 2026 in Korean patent application No. 10-2023-7023061, with English machine translation thereof.

Decision of Refusal dated Jun. 18, 2026, issued in Japanese Patent Application No. 2023-514537, with English machine translation thereof.

* cited by examiner

*Primary Examiner* — Kade Ariani
(74) *Attorney, Agent, or Firm* — Greenblum & Bernstein, P.L.C.

(57) ABSTRACT

The object of the present invention is to provide a production method for β-cryptoxanthin with improved production efficiency. The present invention provides a method for producing β-cryptoxanthin by culturing bacteria of the genus *Paracoccus* at a given dissolved oxygen concentration, wherein the bacteria of the genus *Paracoccus* are bacteria forming yellow to orange colonies; or bacteria whose endogenous crtW gene has been partially or completely deleted or inactivated to lose the ability to produce a functional crtW enzyme.

9 Claims, 1 Drawing Sheet

Specification includes a Sequence Listing.

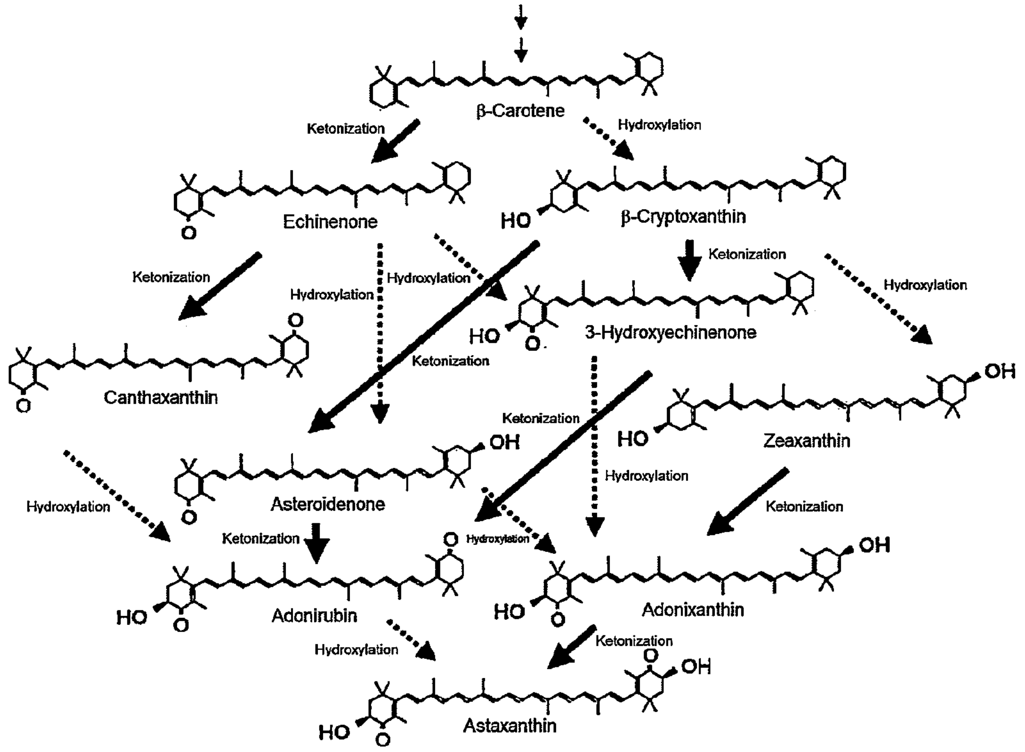
β-Carotene
Ketonization
Hydroxylation
Echinenone
β-Cryptoxanthin
Canthaxanthin
3-Hydroxyechinenone
Zeaxanthin
Asteroidenone
Adonirubin
Adonixanthin
Astaxanthin
HO
OH
O

MICROBE THAT PRODUCES CAROTENOID

TECHNICAL FIELD

The present invention relates to bacteria producing at least one carotenoid selected from the group consisting of β-cryptoxanthin, β-carotene and zeaxanthin or a method for producing the above carotenoid(s). Moreover, the present invention relates to bacteria producing β-cryptoxanthin or a method for producing β-cryptoxanthin.

BACKGROUND ART

Carotenoids are natural pigments useful as feed additives, food additives, pharmaceutical ingredients, etc. Examples of carotenoids include zeaxanthin, β-carotene, β-cryptoxanthin, astaxanthin, canthaxanthin, lycopene, phoenicoxanthin, adonixanthin, echinenone, asteroidenone and 3-hydroxyechinenone, etc.

Among carotenoids, β-cryptoxanthin is contained in citrus fruits and is known to have an antitumor effect (Non-patent Document 1), and has also been reported to be effective in the prevention of osteoporosis (Non-patent Document 2). β-Cryptoxanthin is also known to be used as a health food material or a feed supplement.

Moreover, carotenoids such as zeaxanthin and β-cryptoxanthin accumulate in egg yolk when given to poultry in admixture with feeds for poultry such as chickens. These carotenoids have effective physiological actions, so that egg yolk enriched with these carotenoids is useful as a functional egg.

Patent Document 1 discloses a production method for carotenoids such as zeaxanthin using bacteria of the genus *Paracoccus*. This production method allows the production of not only zeaxanthin but also β-cryptoxanthin. However, the amount of β-cryptoxanthin production per culture solution or relative to the total amount of carotenoids is not sufficient.

Likewise, Patent Document 2 also discloses a production method for zeaxanthin using bacteria of the genus *Paracoccus*. The amount of β-cryptoxanthin production obtained by the method of Patent Document 2 is also not sufficient.

PRIOR ART DOCUMENTS

Patent Documents

Patent Document 1: JP 2005-87097 A
Patent Document 2: WO2011/122616

Non-Patent Documents

Non-patent Document 1: Tsushima M. et al., "Biol. Pharm. Bull." 1995, vol. 18, no. 2, pp. 227-233

Non-patent Document 2: Yamaguchi M et al., "ACS Symp Ser (Am Chem Soc)" 2008, no. 993, pp. 408-418

SUMMARY OF THE INVENTION

Problem to be Solved by the Invention

Under these circumstances, there has been a demand for the development of a production method for β-cryptoxanthin with improved production efficiency.

Means to Solve the Problem

As a result of extensive and intensive efforts, the inventors of the present invention have found a production method for at least one carotenoid selected from the group consisting of β-carotene, β-cryptoxanthin and zeaxanthin, wherein the production efficiency of β-cryptoxanthin is improved. Namely, the present invention is as follows.

[1]

A method for producing at least one carotenoid selected from the group consisting of β-carotene, β-cryptoxanthin and zeaxanthin by culturing bacteria of the genus *Paracoccus*, said method comprising:

adjusting the concentration of dissolved oxygen in a culture solution to 0.8 ppm or less, as measured with a dissolved oxygen electrode, wherein the bacteria of the genus *Paracoccus* are bacteria forming yellow to orange colonies; or bacteria whose endogenous crtW gene has been partially or completely deleted or inactivated to lose the ability to produce a functional crtW enzyme.

[1]'

A method for producing β-cryptoxanthin by culturing bacteria of the genus *Paracoccus*, said method comprising:

adjusting the concentration of dissolved oxygen in a culture solution to 0.8 ppm or less, as measured with a dissolved oxygen electrode, wherein the bacteria of the genus *Paracoccus* are bacteria forming yellow to orange colonies; or bacteria whose endogenous crtW gene has been partially or completely deleted or inactivated to lose the ability to produce a functional crtW enzyme.

[2]

A method for producing at least one carotenoid selected from the group consisting of β-carotene, β-cryptoxanthin and zeaxanthin, said method comprising:

the step of culturing bacteria of the genus *Paracoccus* in a culture solution whose dissolved oxygen concentration is 0.8 ppm or less, wherein the dissolved oxygen concentration of the culture solution is measured with a dissolved oxygen electrode, wherein the bacteria of the genus *Paracoccus* are bacteria forming yellow to orange colonies, e.g., yellow colonies; or bacteria whose endogenous crtW gene has been partially or completely deleted or inactivated to lose the ability to produce a functional crtW enzyme.

[2]'

A method for producing β-cryptoxanthin, said method comprising:

the step of culturing bacteria of the genus *Paracoccus* in a culture solution whose dissolved oxygen concentration is 0.8 ppm or less, wherein the dissolved oxygen concentration of the culture solution is measured with a dissolved oxygen electrode, wherein the bacteria of the genus *Paracoccus* are bacteria forming yellow to orange colonies, e.g., yellow colonies; or bacteria whose endogenous crtW gene has been partially or completely deleted or inactivated to lose the ability to produce a functional crtW enzyme.

[3]

A method for producing at least one carotenoid selected from the group consisting of β-carotene, β-cryptoxanthin and zeaxanthin, said method comprising:

(a) a first culture step where bacteria of the genus *Paracoccus* are allowed to grow in a culture solution, or where bacteria of the genus *Paracoccus* are cultured until the turbidity of the culture solution measured at a measurement wavelength of 610 nm is increased by 5 or more compared to the turbidity at the beginning of the first culture step; and (b) a second culture step where after completion of the first culture step, the bacteria of the genus *Paracoccus* are cultured in a culture solution whose dissolved oxygen concentration is 0.8 ppm or less, wherein the dissolved oxygen concentration of the culture solution is measured with a dissolved oxygen electrode, wherein the bacteria of the genus *Paracoccus* are bacteria forming yellow to orange colonies; or bacteria whose endogenous crtW gene has been partially or completely deleted or inactivated to lose the ability to produce a functional crtW enzyme.

[3]'

A method for producing β-cryptoxanthin, said method comprising:

(a) a first culture step where bacteria of the genus *Paracoccus* are allowed to grow in a culture solution, or where bacteria of the genus *Paracoccus* are cultured until the turbidity of the culture solution measured at a measurement wavelength of 610 nm is increased by 5 or more compared to the turbidity at the beginning of the first culture step; and (b) a second culture step where after completion of the first culture step, the bacteria of the genus *Paracoccus* are cultured in a culture solution whose dissolved oxygen concentration is 0.8 ppm or less, wherein the dissolved oxygen concentration of the culture solution is measured with a dissolved oxygen electrode, wherein the bacteria of the genus *Paracoccus* are bacteria forming yellow to orange colonies; or bacteria whose endogenous crtW gene has been partially or completely deleted or inactivated to lose the ability to produce a functional crtW enzyme.

[4]

The method according to [3] or [3]' above, wherein the culture period in the second culture step is 10 hours or more and 100 hours or less.

[5]

The method according to [3], [3]' or [4] above, wherein the culture period in the first culture step is 10 hours or more and 70 hours or less.

[6]

The method according to any one of [1] to [5] above, wherein the bacteria forming yellow to orange colonies are obtained by selecting yellow to orange colonies generated upon mutagenesis of bacteria of the genus *Paracoccus* that form red colonies.

[6]'

The method according to any one of [1] to [5] above, wherein the bacteria forming yellow to orange colonies are obtained by selecting yellow to orange colonies generated upon mutagenesis of bacteria of the genus *Paracoccus*, and have improved productivity of β-cryptoxanthin when compared to bacteria forming colonies which are not yellow to orange.

[7]

The method according to any one of [1] to [6] above, wherein the endogenous crtW gene comprises a nucleotide sequence at least 90% identical to the nucleotide sequence shown in SEQ ID NO: 1.

[8]

The method according to any one of [1] to [6] above, wherein the crtW enzyme comprises an amino acid sequence at least 90% identical to the amino acid sequence shown in SEQ ID NO: 2.

[9]

The method according to any one of [1] to [8] above, wherein the at least one carotenoid selected from the group consisting of β-carotene, β-cryptoxanthin and zeaxanthin is β-cryptoxanthin.

[10]

Bacteria of the genus *Paracoccus* whose endogenous crtW gene has been partially or completely deleted or inactivated to lose the ability to produce a functional crtW enzyme.

The bacteria of the genus *Paracoccus* according to above are capable of producing at least one carotenoid selected from the group consisting of β-carotene, β-cryptoxanthin and zeaxanthin or are capable of producing β-cryptoxanthin. Moreover, they are capable of forming yellow to orange colonies.

Effects of the Invention

The present invention enables the provision of bacteria producing at least one carotenoid selected from the group consisting of β-carotene, β-cryptoxanthin and zeaxanthin. The present invention enables an improvement in the amount of β-cryptoxanthin production when bacteria producing at least one carotenoid selected from the group consisting of β-carotene, β-cryptoxanthin and zeaxanthin are cultured at a given dissolved oxygen concentration.

BRIEF DESCRIPTION OF THE DRAWINGS

FIG. 1 shows the biosynthetic pathway of astaxanthin.

DESCRIPTION OF EMBODIMENTS

The present invention will be further described in more detail below. The scope of the present invention is not limited by these descriptions, and any embodiments other than those illustrated below may also be carried out with appropriate modifications without departing from the spirit of the invention.

The present invention relates to a production method for carotenoids. The carotenoids produced in the method of the present invention comprise at least one selected from the group consisting of β-carotene, β-cryptoxanthin and zeaxanthin. In one aspect, the carotenoid is β-cryptoxanthin, and the present invention relates to a production method for β-cryptoxanthin. Namely, the present invention relates to a method for producing at least one carotenoid selected from the group consisting of β-carotene, β-cryptoxanthin and zeaxanthin by culturing bacteria producing β-cryptoxanthin (hereinafter also referred to as "the β-cryptoxanthin-producing bacteria of the present invention") at a dissolved oxygen concentration (DO) of 0.8 ppm or less. The β-cryptoxanthin-producing bacteria of the present invention are capable of producing β-cryptoxanthin, β-carotene and zeaxanthin, although they are herein referred to as β-cryptoxanthin-producing bacteria for convenience's sake. In the production method of the present invention, β-cryptoxanthin can be produced in high yield (e.g., 10 mg/l, or more β-cryptoxanthin per culture solution) when compared to culture without adjusting the concentration of dissolved oxygen to 0.8 ppm or less. Thus, the production method of the present invention includes a method for increasing the amount of β-cryptoxanthin production. Moreover, the present invention can also be carried out in yeast strains producing at least one carotenoid selected from the group consisting of β-carotene, β-cryptoxanthin and zeaxanthin. Those skilled in the art would be able to apply the descriptions about bacteria in the specification to yeast strains, as appropriate.

Bacteria for use as the β-cryptoxanthin-producing bacteria of the present invention are not limited in any way as long as they are bacteria producing β-carotene, β-cryptoxanthin or zeaxanthin, as exemplified by bacteria belonging to the genus *Paracoccus* (hereinafter also referred to as "bacteria of the genus *Paracoccus*"). Examples of bacteria of the genus *Paracoccus* include *Paracoccus carotinifaciens, Paracoccus marcusii, Paracoccus haeundaensis, Paracoccus zeaxanthinifaciens*, etc. Among bacteria of the genus *Paracoccus, Paracoccus carotinifaciens* is preferred for use in the present invention. Actual strains of bacteria of the genus *Paracoccus* may be exemplified by *Paracoccus carotinifaciens* strain E-396 (FERM BP-4283) and *Paracoccus* sp. strain A-581-1 (FERM BP-4671). For use in the present invention, these strains forming red colonies are mutated to form yellow to orange colonies, and the thus obtained mutant strains are preferred for use as the β-cryptoxanthin-producing bacteria of the present invention, or alternatively, mutant strains whose endogenous crtW gene has been partially or completely deleted or inactivated to lose the ability to produce a functional crtW enzyme are preferred for use as the β-cryptoxanthin-producing bacteria of the present invention. In bacteria producing astaxanthin, β-cryptoxanthin is not or little produced. Thus, in theory, mutant strains will produce more β-cryptoxanthin than their unmutated parental strain, regardless of the dissolved oxygen concentration during culture.

In one embodiment of the present invention, the β-cryptoxanthin-producing bacteria of the present invention are bacteria forming yellow to orange colonies.

In another embodiment of the present invention, the β-cryptoxanthin-producing bacteria of the present invention are bacteria whose endogenous crtW gene has been partially or completely deleted or inactivated to lose the ability to produce a functional crtW enzyme (β-carotene ketolase).

In another aspect, for use as the β-cryptoxanthin-producing bacteria of the present invention, for example, bacteria producing astaxanthin are mutated to produce more β-cryptoxanthin than the unmutated bacteria, and the thus obtained bacteria of the genus *Paracoccus* may be used. Such bacteria may be exemplified by those showing a higher amount of β-cryptoxanthin production relative to the total amount of carotenoids produced therein than the unmutated bacteria.

Such β-cryptoxanthin-producing bacteria fall within the present invention.

FIG. 1 shows the biosynthetic pathway of astaxanthin, starting from β-carotene. The carotenoids shown in FIG. 1 all have the same number of carbon-carbon double bonds. As seen from the fact that β-carotene has a yellow to orange color while astaxanthin has a red color, the color of carotenoids depends on the presence or absence of a ketone (C═O group) added by the action of the crtW enzyme (β-carotene ketolase). Namely, once the crtW enzyme has functioned normally to introduce a ketone into the β-ionone ring in a carotenoid in a conjugated manner relative to the carbon-carbon double bonds in the carotenoid, the absorption wavelength will shift to a longer wavelength, so that the color of the carotenoid will change from a yellow to orange color to a red color ("ketonization" in FIG. 1). In bacteria producing a functional crtW enzyme (i.e., the crtW enzyme having the ability to add a ketone), adonixanthin, adonirubin, astaxanthin and other carotenoids having one or two ketones in their molecular structure and showing a red color are synthesized, so that their colonies formed also show a red color. On the other hand, bacteria forming yellow to orange colonies do not produce ketone-added carotenoids. This means that a functional crtW enzyme (β-carotene ketolase) is not produced in bacteria forming yellow to orange colonies. Namely, yellow to orange colonies produce carotenoids having no ketone in their molecular structure (i.e., β-cryptoxanthin, β-carotene and zeaxanthin), in theory. Accordingly, β-cryptoxanthin-producing bacteria can be easily selected by picking out yellow to orange colonies.

In the present invention, bacteria producing astaxanthin may be used as a parental strain for obtaining β-cryptoxanthin-producing bacteria. In bacteria producing astaxanthin, the crtW enzyme functions normally, and therefore β-cryptoxanthin is not or little produced. Namely, in bacteria producing astaxanthin, the crtW enzyme responsible for ketone addition functions with a higher priority than hydroxylase (or the reaction rate of the crtW enzyme is significantly faster than the reaction rate of hydroxylase); and hence β-carotene which is a starting material in the biosynthetic pathway of astaxanthin is deemed to be converted into echinenone, but not into β-cryptoxanthin (see FIG. 1). On the other hand, in the strains of the present invention obtained in the Example section, the production of β-cryptoxanthin, β-carotene and zeaxanthin was detected, and the production of astaxanthin was not detected. This indicates that in β-cryptoxanthin-producing bacteria, the crtW enzyme does not function or is significantly less active even when it functions. Actually, the β-cryptoxanthin-producing bacteria obtained in the Example section were found to have a mutation in the crtW enzyme. Such bacteria incapable of producing a functional crtW enzyme fall within β-cryptoxanthin-producing bacteria.

As described above, the β-cryptoxanthin-producing bacteria of the present invention have no crtW enzyme activity; and hence β-carotene which is a starting material in the biosynthetic pathway of astaxanthin is hydroxylated to produce β-cryptoxanthin (see FIG. 1). The produced β-cryptoxanthin may be hydroxylated in the same manner and converted into zeaxanthin. Thus, the β-cryptoxanthin-producing bacteria of the present invention are capable of producing β-cryptoxanthin, β-carotene and zeaxanthin.

To confirm that the crtW enzyme (β-carotene ketolase) in the β-cryptoxanthin-producing bacteria of the present invention does not function (i.e., is not functional) or that the β-cryptoxanthin-producing bacteria are incapable of producing a functional crtW enzyme, the crtW enzyme may be measured for its enzyme activity. For example, to confirm that the crtW enzyme (β-carotene ketolase) in the β-cryptoxanthin-producing bacteria of the present invention does not function (i.e., is not functional) or that the β-cryptoxanthin-producing bacteria are incapable of producing a functional crtW enzyme, measurement by HPLC or other techniques may be conducted to confirm that ketone-added carotenoids, e.g., astaxanthin, adonirubin and adonixanthin are not or little produced. Moreover, to confirm that the crtW enzyme (β-carotene ketolase) in the β-cryptoxanthin-producing bacteria of the present invention does not function (i.e., is not functional) or that the bacteria are incapable of producing a functional crtW enzyme, colonies formed therefrom may be visually confirmed to have a yellow to orange color. Further, to confirm that the crtW enzyme (β-carotene ketolase) in the β-cryptoxanthin-producing bacteria of the present invention does not function (i.e., is not functional) or that the bacteria are incapable of producing a functional crtW enzyme, the bacteria may be analyzed by gene analysis for the nucleotide sequence of the ertW gene or the amino acid sequence of the crtW enzyme.

1. Preparation of β-Cryptoxanthin-Producing Bacteria (1) Mutation

How to obtain the β-cryptoxanthin-producing bacteria of the present invention by mutagenesis of astaxanthin-producing bacteria will be illustrated below.

In the present invention, mutant strains obtained upon mutagenesis of astaxanthin-producing bacteria can be used as the β-cryptoxanthin-producing bacteria of the present invention. Such mutant strains may be exemplified by the mutant strains described in WO2011/122616 and the mutant strains described in JP 2005-87097 A.

Any bacteria may be used as parental strains for mutagenesis as long as they produce astaxanthin. Bacteria of the genus *Paracoccus* are preferred for use. Among bacteria of the genus *Paracoccus* producing astaxanthin, preferred for use are *Paracoccus carotinifaciens, Paracoccus marcusii, Paracoccus haeundaensis* and *Paracoccus zeaxanthinifaciens*, with *Paracoccus carotinifaciens* being particularly preferred for use. Actual strains of bacteria of the genus *Paracoccus* may be exemplified by *Paracoccus carotinifaciens* strain E-396 (FERM BP-4283) and *Paracoccus* sp. strain A-581-1 (FERM BP-4671), and mutant strains thereof are also preferred for use as parental strains. Astaxanthin-producing bacteria used as parental strains for mutagenesis may preferably be exemplified by bacteria in which the nucleotide sequence of DNA corresponding to 16S ribosomal RNA is substantially identical to the nucleotide sequence shown in SEQ ID NO: 7. The DNA nucleotide sequence of SEQ ID NO: 7 is the nucleotide sequence of DNA corresponding to 16S ribosomal RNA in the strain E-396.

As used herein, the phrase "substantially identical" is intended to mean that nucleotide sequences are 90% or more, 91% or more, 92% or more, 93% or more, 94% or more, 95% or more, 96% or more, 97% or more, 98% or more, 99% or more, or 100% identical to each other, in consideration of error frequency in DNA nucleotide sequencing, etc.

Any technique may be used for mutagenesis of astaxanthin-producing bacteria, as long as it induces a mutation(s). For example, it is possible to use chemical techniques using a mutagen such as N-methyl-N'-nitro-N-nitrosoguanidine (NTG) or ethyl methanesulfonate (EMS), physical techniques such as ultraviolet irradiation and X-ray irradiation, or biological techniques based on gene recombination or transposon, etc. Alternatively, naturally occurring spontaneous mutations are also possible for this purpose. Such mutagenesis may be conducted once, or alternatively, may be repeated twice or more such that mutants highly producing astaxanthin are obtained by this mutagenesis, and the resulting mutants are further subjected to mutagenesis, by way of example.

(2) Mutation in Endogenous crtW Gene

In one aspect, the β-cryptoxanthin-producing bacteria of the present invention are incapable of producing a functional crtW enzyme, because their endogenous crtW gene is partially or completely deleted or inactivated. Such deletion or inactivation may target at least one of the coding sequence of the crtW gene and a promoter for expression of the crtW gene. For example, deletion or inactivation of the crtW gene includes a missense mutation (i.e., a mutation to another amino acid by nucleotide substitution), a nonsense mutation (i.e., a mutation to a termination codon), a frameshift mutation (i.e., nucleotide insertion and/or deletion within a gene), an in-frame mutation, etc., but is not limited thereto, as long as deletion or inactivation is sufficient to lose the ability to produce a functional crtW enzyme.

As used herein, the term "crtW enzyme" or "β-carotene ketolase" is an enzyme involved in the reaction for introducing ketones into the terminal ring structures (β-ionone rings) of carotenoids. The endogenous crtW gene and crtW enzyme in bacteria (e.g., bacteria of the genus *Paracoccus*) have been known to those skilled in the art, and may be used as appropriate in the present invention by those skilled in the art. By way of example, the nucleotide sequence (crtW gene) and amino acid sequence of the crtW enzyme in *Paracoccus carotinifaciens* are shown in SEQ ID) NO: 1 and SEQ ID NO: 2, respectively.

In a further embodiment, the crtW gene may have a nucleotide sequence at least 80% identical to SEQ ID NO: 1, e.g., at least 85%, 90%, 95%, 96%, 97%, 98% or 99% or more identical to SEQ ID NO: 1. In another embodiment, the ertW gene may have a nucleotide sequence encoding an amino acid sequence at least 80% identical to SEQ ID NO: 2, e.g., at least 85%, 90%, 95%, 96%, 97%, 98% or 99% or more identical to SEQ ID NO: 2. In yet another embodiment, the crtW enzyme may have an amino acid sequence encoded by a nucleotide sequence at least 80% identical to SEQ ID NO: 1, e.g., at least 85%, 90%, 95%, 96%, 97%, 98% or 99% or more identical to SEQ ID NO: 1. In still yet another embodiment, the crtW enzyme may have an amino acid sequence at least 80% identical to SEQ ID NO: 2, e.g., at least 85%, 90%, 95%, 96%, 97%, 98% or 99% or more identical to SEQ ID NO: 2. Proteins encoded by these mutated crtW genes or these crtW enzymes have β-carotene ketolase activity.

Amino acids involved in the function of the crtW enzyme have been known. For example, H65 (histidine at position 65 of the amino acid sequence), H69, H103, H106, H107, H184, H218, H219, H221, H222, D117, F130 and other amino acids in the crtW enzyme have been known to be completely or partially required for crtW enzyme activity (Rick et al., Appl Environ Microbiol. 2006 September; 72(9):5829-37). Rick et al. have reported that the production ratio of zeaxanthin was increased in bacteria whose crtW enzyme had been mutated. Thus, when these amino acids are mutated to amino acids of different nature, the crtW enzyme completely or partially loses its function, and bacteria are expected to produce β-cryptoxanthin. In one aspect of the present invention, deletion or inactivation of the crtW gene includes genetic mutations such that these amino acids are mutated to alanine or amino acids of different nature. Mutations to amino acids of different nature include a mutation from a basic amino acid (e.g., histidine) to a neutral amino acid (e.g., tyrosine) or an acidic amino acid, a mutation from an acidic amino acid (e.g., aspartic acid) to a neutral amino acid or a basic amino acid, and a mutation from a neutral amino acid (phenylalanine which is an aromatic amino acid) to an acidic amino acid or a basic amino acid.

In one aspect of the present invention, the crtW gene partially or completely deleted or inactivated in the present invention has, for example, but not limited to, the nucleotide sequence of SEQ ID NO: 3 or 5 or a nucleotide sequence encoding the amino acid sequence of SEQ ID NO: 4 or 6. In another aspect of the present invention, the crtW enzyme partially or completely deleted or inactivated in the present invention has, for example, but not limited to, an amino acid sequence encoded by the nucleotide sequence of SEQ ID NO: 3 or 5 or the amino acid sequence of SEQ ID NO: 4 or 6. It should be noted that as a result of gene analysis, the strain ZXA-3 was confirmed to have a mutation at the same position as the strain ZXA-23. The nucleotide sequence and amino acid sequence of crtW in the strain ZXA-3 are shown in SEQ ID NO: 5 and SEQ ID NO: 6, respectively.

TABLE 1-1

| Table 1 Nucleotide sequence and amino acid sequence of crtW |
|---|
| SEQ ID NO: 1 (strain E-396): wild-type |
| ATGAGCGCACATGCCCTGCCCAAGGCAGATCTGACCGCCACCAGTTTGAT<br>CGTCTCGGGCGGCATCATCGCCGCGTGGCTGGCCCTGCATGTGCATGCGC<br>TGTGGTTTCTGGACGCGGCGGCGCATCCCATCCTGGCGGTCGCGAATTTC<br>CTGGGGCTGACCTGGCTGTCGGTCGGTCTGTTCATCATCGCGCATGACGC<br>GATGCATGGGTCGGTCGTGCCGGGGCGCCCGCGCGCCAATGCGGCGATGG<br>GCCAGCTTGTCCTGTGGCTGTATGCCGGATTTTCCTGGCGCAAGATGATC<br>GTCAAGCACATGGCCCATCATCGCCATGCCGGAACCGACGACGACCCAGA<br>TTTCGACCATGGCGGCCCGGTCCGCTGGTACGCCCGCTTCATCGGCACCT<br>ATTTCGGCTGGCGCGAGGGGCTGCTGCTGCCCGTCATCGTGACGGTCTAT<br>GCGCTGATGTTGGGGGATCGCTGGATGTACGTGGTCTTCTGGCCGTTGCC<br>GTCGATCCTGGCGTCGATCCAGCTGTTCGTGTTCGGCACTTGGCTGCCGC<br>ACCGCCCCGGCCACGACGCGTTCCCGGACCGCCACAATGCGCGGTCGTCG<br>CGGATCAGCGACCCCGTGTCGCTGCTGACCTGCTTTCACTTTGGCGGTTA<br>TCATCACGAACACCACCTGCACCCGACGGTGCCTTGGTGGCGCCTGCCCA<br>GCACCCGCACCAAGGGGGACACCGCATGA |
| SEQ ID NO: 2 (strain E-396): wild-type |
| MSAHALPKADLTATSLIVSGGIIAAWLALHVHALWFLDAAAHPILAVANF<br>LGLTWLSVGLFIIAHDAMHGSVVPGRPRANAAMGQLVLWLYAGFSWRKMI<br>VKHMAHHRHAGTDDDPDFDHGGPVRWYARFIGTYFGWREGLLLPVIVTVY<br>ALMLGDRWMYVVFWPLPSILASIQLFVFGTWLPHRPGHDAFPDRHNARSS<br>RISDPVSLLTCFHFGGYHHEHHLHPTVPWWRLPSTRIKGDTA |
| SEQ ID NO: 3 (strain BC-60, strain BC-65): comprising a mutation from a tryptophan-encoding codon (ugg) to a stop codon (uga) |
| ATGAGCGCACATGCCCTGCCCAAGGCAGATCTGACCGCCACCAGTTTGAT<br>CGTCTCGGGCGGCATCATCGCCGCGTGGCTGGCCCTGCATGTGCATGCGC<br>TGTGGTTTCTGGACGCGGCGGCGCATCCCATCCTGGCGGTCGCGAATTTC<br>CTGGGGCTGACCTGGCTGTCGGTCGGTCTGTTCATCATCGCGCATGACGC<br>GATGCATGGGTCGGTCGTGCCGGGGCGCCCGCGCGCCAATGCGGCGATGG<br>GCCAGCTTGTCCTGTGGCTGTATGCCGGATTTTCCTGGCGCAAGATGATC<br>GTCAAGCACATGGCCCATCATCGCCATGCCGGAACCGACGACGACCCAGA<br>TTTCGACCATGGCGGCCCGGTCCGCTGGTACGCCCGCTTCATCGGCACCT<br>ATTTCGGCTGGCGCGAGGGGCTGCTGCTGCCCGTCATCGTGACGGTCTAT<br>GCGCTGATGTTGGGGGATCGCTGGATGTACGTGGTCTTCTGGCCGTTGCC<br>GTCGATCCTGGCGTCGATCCAGCTGTTCGTGTTCGGCACTTGGCTGCCGC<br>ACCGCCCCGGCCACGACGCGTTCCCGGACCGCCACAATGCGCGGTCGTCG<br>CGGATCAGCGACCCCGTGTCGCTGCTGACCTGCTTTCACTTTGGCGGTTA<br>TCATCACGAACACCACCTGCACCCGACGGTGCCTTGGTGACGCCTGCCCA<br>GCACCCGCACCAAGGGGGACACCGCATGA |
| SEQ ID NO: 4 (strain BC-60, strain BC-65) |
| MSAHALPKADLTATSLIVSGGIIAAWLALHVHALWFLDAAAHPILAVANF<br>LGLTWLSVGLFIIAHDAMHGSVVPGRPRANAAMGQLVLWLYAGFSWRKMI<br>VKHMAHHRHAGTDDDPDFDHGGPVRWYARFIGTYFGWREGLLLPVIVTVY<br>ALMLGDRWMYVVFWPLPSILASIQLFVFGTWLPHRPGHDAFPDRHNARSS<br>RISDPVSLLTCFHFGGYHHEHHLHPTVPW |

TABLE 1-2

| SEQ ID NO: 5 (strain ZXA-23): comprising a mutation from a histidine-encoding codon (cau) to a tyrosine-encoding codon (uau) |
|---|
| ATGAGCGCACATGCCCTGCCCAAGGCAGATCTGACCGCCACCAGTTTGAT<br>CGTCTCGGGCGGCATCATCGCCGCGTGGCTGGCCCTGCATGTGCATGCGC<br>TGTGGTTTCTGGACGCGGCGGCGCATCCCATCCTGGCGGTCGCGAATTTC<br>CTGGGGCTGACCTGGCTGTCGGTCGGTCTGTTCATCATCGCGTATGACGC<br>GATGCATGGGTCGGTCGTGCCGGGGCGCCCGCGCGCCAATGCGGCGATGG<br>GCCAGCTTGTCCTGTGGCTGTATGCCGGATTTTCCTGGCGCAAGATGATC<br>GTCAAGCACATGGCCCATCATCGCCATGCCGGAACCGACGACGACCCAGA |

TABLE 1-2-continued

| |
|---|
| TTTCGACCATGGCGGCCCGGTCCGCTGGTACGCCCGCTTCATCGGCACCT<br>ATTTCGGCTGGCGCGAGGGGCTGCTGCTGCCCGTCATCGTGACGGTCTAT<br>GCGCTGATGTTGGGGGATCGCTGGATGTACGTGGTCTTCTGGCCGTTGCC<br>GTCGATCCTGGCGTCGATCCAGCTGTTCGTGTTCGGCACTTGGCTGCCGC<br>ACCGCCCCGGCCACGACGCGTTCCCGGACCGCCACAATGCGCGGTCGTCG<br>CGGATCAGCGACCCCGTGTCGCTGCTGACCTGCTTTCACTTTGGCGGTTA<br>TCATCACGAACACCACCTGCACCCGACGGTGCCTTGGTGGCGCCTGCCCA<br>GCACCCGCACCAAGGGGGACACCGCATGA |
| SEQ ID NO: 6 (strain ZXA-23): comprising a mutation from histidine to tyrosine in the amino acid at position 65 |
| MSAHALPKADLTATSLIVSGGIIAAWLALHVHALWFLDAAAHPILAVANF<br>LGLTWLSVGLFIIAYDAMHGSVVPGRPRANAAMGQLVLWLYAGFSWRKMI<br>VKHMAHHRHAGTDDDPDFDHGGPVRWYARFIGTYFGWREGLLLPVIVTVY<br>ALMLGDRWMYVVFWPLPSILASIQLFVFGTWLPHRPGHDAFPDRHNARSS<br>RISDPVSLLTCFHFGGYHHEHHLHPTVPWWRLPSTRTKGDTA |

The activity of the crtW enzyme may be determined indirectly, for example, by gene sequencing. In this way, a mutation inducing partial or complete deletion or inactivation can be easily identified.

As used herein, the phrase "lose the ability to produce a functional crtW enzyme" or "incapable of producing a functional crtW enzyme" is intended to mean having no or substantially no crtW enzyme activity. In more detail, the phrase "lose the ability to produce a functional crtW enzyme" or "incapable of producing a functional crtW enzyme" is intended to mean having crtW enzyme activity which is less than 20% of the crtW enzyme activity in astaxanthin-producing bacteria. For example, the crtW enzyme activity in the β-cryptoxanthin-producing bacteria of the present invention is less than 20%, less than 15%, preferably less than 10%, more preferably less than 5%, even more preferably less than 1% of the wild-type crtW enzyme activity. As described above, it is most preferred that bacteria incapable of producing a functional crtW enzyme have undetectable crtW enzyme activity, or substantially or completely lose their crtW enzyme activity.

The term "crtW enzyme activity" refers to the ability to add a ketone to a carotenoid, and examples include the activity to convert β-carotene into echinenone, the activity to convert echinenone into canthaxanthin, the activity to convert β-cryptoxanthin into asteroidenone, the activity to convert β-cryptoxanthin into 3-hydroxyechinenone, the activity to convert 3-hydroxyechinenone into adonirubin, the activity to convert zeaxanthin into adonixanthin, the activity to convert asteroidenone into adonirubin, and the activity to convert adonixanthin into astaxanthin.

In the present invention, bacteria incapable of producing a functional crtW enzyme may be obtained by any means known in the art using molecular biological methodology, or may be obtained by screening of mutants obtained upon the above mutagenesis. The endogenous crtW gene or a promoter for expression of crtW in the β-cryptoxanthin-producing bacteria of the present invention has been partially or completely deleted or inactivated to lose the ability to produce a functional crtW enzyme. For gene disruption, techniques known in the art can be used. For example, the coding region of the endogenous crtW gene may be completely or partially removed or inactivated, or the promoter region may be completely or partially removed or inactivated by mutagenesis. Alternatively, a knock-in mutation may be introduced into the endogenous crtW gene to thereby disrupt the endogenous coding sequence. For example, an immature termination codon or a frameshift mutation may be introduced for this purpose. As long as no functional ertW enzyme is completely or substantially produced, the crtW gene may comprise a missense mutation or a nonsense mutation.

Bacteria incapable of producing a functional crtW enzyme as mentioned above also fall within the β-cryptoxanthin-producing bacteria of the present invention, and may be prepared by those skilled in the art on the basis of common knowledge in the art.

(3) The β-cryptoxanthin-producing bacteria of the present invention can be obtained on the basis of the descriptions in (1) and (2) above. In theory, the β-cryptoxanthin-producing bacteria of the present invention will produce more β-cryptoxanthin than unmutated bacteria (e.g., their parental strain), regardless of the dissolved oxygen concentration during culture.

The β-cryptoxanthin-producing bacteria of the present invention are expected to achieve a higher amount of β-cryptoxanthin production relative to the total amount of carotenoids produced therein than unmutated bacteria. The amount of β-cryptoxanthin production may be measured by analyzing the amount of carotenoids in the culture solution obtained upon culturing the bacteria of interest.

For example, culture is carried out in a medium containing components which are required for the growth of the intended producing bacteria to produce carotenoids. Culture may be accomplished in any manner, such as shaking culture, aeration spinner culture, etc. in test tubes, flasks or the like. Any technique may be used for analysis of carotenoid compounds, as long as it allows the separation and detection of carotenoid compounds. For example, it is possible to use high performance liquid chromatography, thin-layer chromatography, paper chromatography, etc. The β-cryptoxanthin-producing bacteria of the present invention can be obtained, for example, by picking out mutant strains with a higher production ratio of β-cryptoxanthin relative to the total amount of carotenoids. The total amount of carotenoids refers to the sum of the amounts of carotenoids, such as astaxanthin, canthaxanthin, adonixanthin, β-carotene, echinenone, zeaxanthin, β-cryptoxanthin, 3-hydroxyechinenone, asteroidenone, adonirubin and the like. The ratio of β-cryptoxanthin is minimally required to be higher than the production ratio of β-cryptoxanthin in unmutated bacteria (e.g., their parental strain). For example, it is possible to pick out mutant strains showing a β-cryptoxanthin ratio of preferably 20% (w/w) or more, more preferably 40% (w/w) or more, even more preferably 60% (w/w) or more, relative to the total amount of carotenoids produced therein. In the present invention, bacteria producing astaxanthin may be used as unmutated bacteria, but bacteria producing astaxanthin generally produce no or little β-cryptoxanthin. By way of example, the amounts of carotenoids produced upon culture of astaxanthin-producing bacteria belonging to the genus *Paracoccus* are shown below. The culture of bacteria and the measurement of carotenoids were conducted in the same manner as described in the Example section.

TABLE 2

Carotenoid production in astaxanthin-producing bacteria

| Dissolved oxygen concentration (DO) [ppm] | Culture period [h] | β-Carotene per culture solution [mg/L] | β-Cryptoxanthin per culture solution [mg/L] | Zeaxanthin per culture solution [mg/L] | Astaxanthin per culture solution [mg/L] |
|---|---|---|---|---|---|
| 2.0 | 142 | 26.8 | 0 | 3.1 | 122.8 |
| 1.6 | 113 | 49.6 | 0 | 0 | 228.9 |

The β-cryptoxanthin-producing bacteria of the present invention can be efficiently selected by being grown to form colonies on agar medium after mutagenesis in (1) or (2) above to select yellow to orange colonies. Since bacteria producing β-cryptoxanthin form yellow to orange colonies, desired bacteria producing β-cryptoxanthin (i.e., the β-cryptoxanthin-producing bacteria of the present invention) can be efficiently selected by picking out yellow to orange colonies. To confirm that the β-cryptoxanthin-producing bacteria of the present invention produce β-cryptoxanthin, the selected colonies may be cultured in test tubes or flasks, etc., and quantified for β-cryptoxanthin to determine the amount of β-cryptoxanthin production. The color of colonies to be picked out is yellow, orange, or a color between yellow and orange, which is clearly different from the red color shown by colonies of bacteria producing astaxanthin, etc. Thus, this method allows the simple and accurate selection of desired bacteria.

In another aspect of the present invention, the β-cryptoxanthin-producing bacteria of the present invention are bacteria whose endogenous crtW gene has been partially or completely deleted or inactivated, when compared to unmutated bacteria (e.g., their parental strain), to thereby lose the ability to produce a functional crtW enzyme. To confirm that the endogenous crtW gene has been partially or completely deleted or inactivated, the crtW gene contained in the bacteria may be analyzed. For example, analysis may be accomplished by using known techniques such as gene sequencing, RT-PCR analysis, real-time PCR analysis, Southern blotting analysis, Northern blotting analysis, etc. Likewise, to confirm loss of the ability to produce a functional crtW enzyme, crtW enzyme expression may be confirmed by Western blotting analysis, immunostaining, etc., or alternatively, crtW enzyme activity may be measured, e.g., by measuring the amount of keto-carotenoid production, etc.

2. Production Method of the Present Invention

The present invention relates to a method for producing at least one carotenoid selected from the group consisting of β-carotene, β-cryptoxanthin and zeaxanthin by culturing the β-cryptoxanthin-producing bacteria of the present invention at a given dissolved oxygen concentration. There is disclosed herein a method for producing at least one carotenoid selected from the group consisting of β-carotene, β-cryptoxanthin and zeaxanthin by culturing the β-cryptoxanthin-producing bacteria of the present invention, said method comprising adjusting the concentration of dissolved oxygen in a culture solution to 0.8 ppm or less, or a method for producing at least one carotenoid selected from the group consisting of β-carotene, β-cryptoxanthin and zeaxanthin, said method comprising the step of culturing the β-cryptoxanthin-producing bacteria of the present invention in a culture solution whose dissolved oxygen concentration is 0.8 ppm or less. The carotenoids produced in the production method of the present invention are one or more carotenoids selected from β-carotene, β-cryptoxanthin and zeaxanthin. In another aspect of the present invention, the carotenoid produced in the production method of the present invention is β-cryptoxanthin.

When the concentration of dissolved oxygen is adjusted to 0.8 ppm or less during culture of the β-cryptoxanthin-producing bacteria of the present invention, β-cryptoxanthin is efficiently produced, thus resulting in a higher amount of β-cryptoxanthin production per culture solution or a higher β-cryptoxanthin concentration relative to the total amount of carotenoids produced. In another aspect of the present invention, β-cryptoxanthin and β-carotene are efficiently produced.

For efficient production of β-cryptoxanthin, the concentration of dissolved oxygen in a culture solution is adjusted to 0.8 ppm or less, preferably 0.7 ppm or less, more preferably 0.6 ppm or less, even more preferably 0.5 ppm or less, and most preferably 0.4 ppm or less. Upon culture under conditions where the concentration of dissolved oxygen in a culture solution is 0.8 ppm, the amount of β-cryptoxanthin per culture solution can be increased.

As used herein, values expressed in "%" and "ppm" are by volume, and "1 ppm" has the same meaning as "1 mg/L." The mass of a culture solution is almost equal to the mass of water with the same volume, and when both are equal to each other, values expressed in "ppm" are by mass, and "1 ppm" has the same meaning as "1 mg/kg."

Dissolved oxygen in a culture solution is measured with a dissolved oxygen electrode. As a dissolved oxygen electrode, for example, a product of B. E. Marubishi Co., Ltd., Japan (model number: OX-2500) may be used for measurement. A dissolved oxygen electrode is corrected assuming that the amount of oxygen when the dissolved oxygen electrode is allowed to stand in the air for 5 minutes is set to 100%, and the amount of oxygen when the dissolved oxygen electrode is allowed to stand in a 50 g/L aqueous sodium sulfite solution for 5 minutes is set to 0%. In water under the air, the dissolved oxygen concentration reaches the equilibrium state at 8 ppm, so that the amount of oxygen (=100%) when the dissolved oxygen electrode is allowed to stand in the air for 5 minutes is calculated to be 8 ppm dissolved oxygen concentration in water.

The adjustment of the dissolved oxygen concentration may be controlled in a manner commonly used for culture. For example, the flow rate of air or oxygen supplied into a culture tank may be adjusted automatically in response to the concentration of dissolved oxygen in a culture solution measured with a dissolved oxygen electrode, or the rotational speed or frequency of an impeller may be regulated automatically in response to the concentration of dissolved oxygen in a culture solution measured with a dissolved oxygen electrode, or alternatively, the aeration volume and the rotational speed or frequency may both be adjusted.

The medium used for culture in this method (hereinafter also referred to as "β-cryptoxanthin production medium") is not limited in any way, as long as the β-cryptoxanthin-producing bacteria of the present invention grow and produce β-cryptoxanthin when cultured by adjusting the concentration of dissolved oxygen in the culture solution to 0.8 ppm or less. Preferred for use is a medium containing a carbon source, a nitrogen source, inorganic salts and optionally vitamins, etc.

Examples of a carbon source include sugars (e.g., glucose, sucrose, lactose, fructose, trehalose, mannose, mannitol and maltose), organic acids (e.g., acetic acid, fumaric acid, citric acid, propionic acid, malic acid, malonic acid and pyruvic acid), alcohols (e.g., ethanol, propanol, butanol, pentanol, hexanol, isobutanol and glycerol), and fats or oils (e.g., soybean oil, rice bran oil, olive oil, corn oil, sesame oil and linseed oil), with glucose or sucrose being preferred for use. Moreover, these carbon sources may be used either alone or in combination. The amount of a carbon source to be added to the medium before culture (initial medium) will vary depending on the type of carbon source and may be adjusted as appropriate, but it is usually 1 to 100 g, preferably 2 to 50 g, per liter of the medium. Moreover, these carbon sources are not only added to the initial medium, but preferably may also be further supplied sequentially or continuously during culture.

As used herein, when the word "to" is used to express a numerical range, the lower and upper limits are inclusive, unless otherwise specified. For example, in the case of the numerical range "1 to 100," its lower limit "1" and its upper limit "100" are both inclusive. Namely, "1 to 100" is synonymous with "equal to or greater than 1 and equal to or less than 100."

Examples of an inorganic nitrogen source include ammonium salts (e.g., ammonium nitrate, ammonium sulfate, ammonium chloride, ammonium phosphate), nitrate salts (e.g., potassium nitrate), ammonia and urea, which may be used either alone or in combination. The amount to be added will vary depending on the type of nitrogen source and may be adjusted as appropriate, but it is usually 0.1 g to 20 g, preferably 0.2 to 10 g, per liter of the medium.

Examples of an organic nitrogen source include corn steep liquor (including filtered corn steep liquor), Pharmamedia, soybean meal, soybean flour, peanut meal, sodium glutamate, distillers's solubles and dry yeast, which may be used either alone or in combination. The concentration to be added will vary depending on the type of nitrogen source and may be adjusted as appropriate, but it is usually 0 to 80 g/L, preferably 0 to 30 g/L, in the medium.

These inorganic and organic nitrogen sources are normally added to the initial medium, but preferably may also be further supplied sequentially or continuously.

Examples of inorganic salts include phosphate salts (e.g., potassium dihydrogen phosphate, dipotassium hydrogen phosphate, disodium hydrogen phosphate), magnesium salts (e.g., magnesium sulfate, magnesium chloride), iron salts (e.g., iron sulfate, iron chloride), calcium salts (e.g., calcium chloride, calcium carbonate), sodium salts (e.g., sodium carbonate, sodium chloride), manganese salts (e.g., manganese sulfate), cobalt salts (e.g., cobalt chloride), copper salts (e.g., copper sulfate), zinc salts (e.g., zinc sulfate), molybdenum salts (e.g., sodium molybdate), nickel salts (e.g., nickel sulfate), selenium salts (e.g., sodium selenate), boric acid and potassium iodide, which may be used either alone or in combination. The amount to be added will vary depending on the type of inorganic salt and may be adjusted as appropriate, but it is usually 0.0001 to 15 g per liter of the medium. A preferred concentration in the medium is 0.02 to 15 g/L for phosphate salts, magnesium salts, calcium salts, sodium salts and iron salts, and is 0.1 to 15 mg/L for manganese salts, cobalt salts, copper salts, zinc salts, molybdenum salts, nickel salts, selenium salts, boric acid, potassium iodide and so on. These inorganic salts are normally added to the initial medium, but may also be further supplied sequentially or continuously.

Examples of vitamins available for use include cyanocobalamin, riboflavin, pantothenic acid, pyridoxine, thiamine, ascorbic acid, folic acid, niacin, p-aminobenzoic acid, inositol, choline, biotin and so on. The ratio to be added will vary depending on the type of vitamin and may be adjusted as appropriate, but it is usually 0.001 to 1000 mg, preferably 0.01 to 100 mg, per liter of the medium. These vitamins are normally added to the initial medium, but may also be further supplied sequentially or continuously.

In the present invention, a defoaming agent may preferably be used to avoid bubbling of the culture solution. Such a defoaming agent may be of any type as long as it has the ability to prevent bubble formation or to break the bubbles formed and is also less inhibitory against the intended producing bacteria. Examples include alcohol-based defoaming agents, polyether-based defoaming agents, ester-based defoaming agents, fatty acid-based defoaming agents, silicon-based defoaming agents, sulfonic acid-based defoaming agents and so on. The amount of a defoaming agent to be added will vary depending on the type of defoaming agent and may be adjusted as appropriate, but it is usually 0.01 g to 10 g per liter of the medium.

Such a defoaming agent is normally added to the initial medium before sterilization, and may further be added continuously or intermittently during culture. For addition of a defoaming agent during culture, the defoaming agent may be automatically added upon detection of bubbles with a sensor, or may be added at given time intervals with a programmed timer, or may be added in response to the growth rate in admixture with any component to be fed, e.g., a carbon source, a nitrogen source or a pH adjuster, by way of example. The defoaming agent added to the initial medium and the defoaming agent added to the culture solution during culture may be either of the same or different type, depending on the intended effect.

In this method, the initial pH of the medium is adjusted to 2 to 12, preferably 6 to 9, more preferably 6.5 to 8.0. It is preferable to also maintain the medium pH within the above range during culture. For maintenance of the medium pH, it is preferred that the pH of the culture solution is measured on-line with a pH electrode equipped within a fermenter to automatically supply an alkali. Examples of a pH adjuster include aqueous sodium hydroxide, aqueous potassium hydroxide, aqueous sodium carbonate, aqueous ammonia, ammonia gas, aqueous sulfuric acid, or any mixture thereof.

In this method, the medium is sterilized before use in bacterial culture. Sterilization may be accomplished as appropriate by those skilled in the art. For example, the medium in an appropriate container may be sterilized by heating in an autoclave. Alternatively, the medium may be sterilized by filtration through a sterile filter. Alternatively, the medium may be sterilized by jacket heating and steam blowing. A carbon source such as glucose may be sterilized separately because it will be browned when sterilized by heating together with other medium components. Vitamins and trace metals may be sterilized by heating together with the main medium, but may be sterilized separately to avoid deactivation or precipitation.

In this method, β-cryptoxanthin-producing bacteria are inoculated into the β-cryptoxanthin production medium prepared as above and cultured under predetermined conditions. Inoculation may be accomplished as follows: strains are allowed to grow as appropriate by seed culture in test tubes, flasks or fermenters, etc., and the resulting culture solutions are each added to the β-cryptoxanthin production medium (main culture).

Seed culture may be conducted prior to the main culture, and seed culture may be accomplished in accordance with techniques known to those skilled in the art. Any medium may be used for seed culture as long as it is a medium allowing the good growth of β-cryptoxanthin-producing bacteria.

Culture is conducted in an appropriate culture vessel. Such a culture vessel may be selected as appropriate depending on the culture volume and is exemplified by test tubes, flasks, fermenters, etc.

The culture temperature is set to, for example, 15° C. to 40° C., preferably 20° C. to 35° C., and more preferably 25° C. to 32° C. Moreover, the culture period may be set to usually 1 to 20 days, preferably 1 to 12 days, more preferably 2 to 8 days, and particularly preferably 3 to 7 days.

The β-cryptoxanthin-producing bacteria of the present invention are cultured under aerobic conditions. Culture under aerobic conditions may be exemplified by shaking culture or aeration spinner culture, etc. In the main culture, the concentration of dissolved oxygen is adjusted as described above.

Culture is conducted under aerobic conditions from the beginning of the main culture until the β-cryptoxanthin-producing bacteria of the present invention grow well (first culture step). Culture under aerobic conditions (first culture step) is conducted for 5 to 80 hours, preferably 10 to 70 hours, 10 to 60 hours, more preferably 10 to 50 hours, even more preferably 10 to 40 hours, even still more preferably 10 to 36 hours, after the beginning of culture in the β-cryptoxanthin production medium. Alternatively, the first culture step may be conducted for 20 to 80 hours, 20 to 60 hours, 20 to 40 hours, or 20 to 36 hours. The concentration of dissolved oxygen in this step is 0.8 ppm or more, for example, 1 ppm or more, preferably 1.5 ppm or more, and more preferably 2 ppm or more.

In one aspect of the present invention, the first culture step may be continued until the turbidity of the culture solution measured at a measurement wavelength of 610 nm is increased by at least 5 or more compared to the turbidity at the beginning of the first culture step. The increment of turbidity from the beginning of the first culture step is at least 5 or more, preferably 10 or more, more preferably 11 or more, 12 or more, 13 or more, 14 or more, 15 or more, 16 or more, 17 or more, 18 or more, 19 or more, or 20 or more. For example, when the bacteria are cultured for 10 to 36 hours, the rate of increase in turbidity is high, and the increment of turbidity in this case is about 20 to 400.

Moreover, in the first culture step, the concentration of dissolved oxygen is not maintained at 0.8 ppm or less, as described above, and the concentration of dissolved oxygen is gradually reduced from the beginning of culture, and reaches the reduction peak and then turns to increase. In another aspect of the present invention, the first culture step may be continued until the concentration of dissolved oxygen becomes lowest.

After growing well, the β-cryptoxanthin-producing bacteria of the present invention are cultured under conditions where the concentration of dissolved oxygen in the culture solution is 0.8 ppm or less, whereby β-cryptoxanthin can be efficiently produced (second culture step). The β-cryptoxanthin-producing bacteria of the present invention do not grow well when cultured under 0.8 ppm or less dissolved oxygen before growing well, which may lead to a reduced yield of β-cryptoxanthin. Thus, after the β-cryptoxanthin-producing bacteria of the present invention are allowed to grow in the culture solution, the bacteria are cultured in a culture solution with 0.8 ppm or less dissolved oxygen, whereby β-cryptoxanthin can be efficiently produced. After the concentration of dissolved oxygen is adjusted to 0.8 ppm or less, the β-cryptoxanthin-producing bacteria of the present invention can be cultured for 5 to 200 hours, preferably 10 to 150 hours, more preferably 10 hours to 100 hours, 20 to 80 hours, 30 to 60 hours, or 40 to 60 hours, for example, 40 hours. During this period of culture, the concentration of dissolved oxygen is maintained at 0.8 ppm or less.

Thus, the production method for β-cryptoxanthin of the present invention may comprise a second culture step of:

(i) adjusting the concentration of dissolved oxygen to 0.8 ppm or less in the culture solution of the β-cryptoxanthin-producing bacteria of the present invention which have been allowed to grow or the β-cryptoxanthin-producing bacteria of the present invention whose culture solution's turbidity measured at a measurement wavelength of 610 nm has been increased by 5 or more compared to the turbidity at the beginning of the first culture step; and (ii) culturing the above β-cryptoxanthin-producing bacteria of the present invention in the culture solution whose dissolved oxygen concentration is 0.8 ppm or less. The above method allows the production of at least one carotenoid selected from the group consisting of β-carotene, β-cryptoxanthin and zeaxanthin.

In another aspect of the present invention, the production method for β-cryptoxanthin of the present invention may comprise:

(a) a first culture step where bacteria of the genus *Paracoccus* are allowed to grow in a culture solution, or where the β-cryptoxanthin-producing bacteria of the present invention are cultured until the turbidity of the culture solution measured at a measurement wavelength of 610 nm is increased by 5 or more compared to the turbidity at the beginning of the first culture step; and (b) a second culture step where after completion of the first culture step, the β-cryptoxanthin-producing bacteria of the present invention are cultured in a culture solution whose dissolved oxygen concentration is 0.8 ppm or less. The above method allows the production of at least one carotenoid selected from the group consisting of β-carotene, β-cryptoxanthin and zeaxanthin.

When the β-cryptoxanthin-producing bacteria of the present invention are cultured as described above, β-cryptoxanthin can be efficiently produced. The amount of β-cryptoxanthin production in the culture solution finally obtained after completion of the culture may be 10 mg/L or more, 15 mg/L or more, or 20 mg/L or more, per culture solution. Likewise, the concentration of β-cryptoxanthin produced in the culture solution finally obtained after completion of the culture may be 3.5% by mass or more, 4% by mass or more, or 4.5% by mass or more, relative to the total amount of carotenoids.

Carotenoids in the culture solution obtained by culturing the β-cryptoxanthin-producing bacteria of the present invention, or carotenoids collected from the culture solution may be quantified, for example, by high performance liquid chromatography.

The production method of the present invention may further comprise the step of collecting, from the cultured product, at least one carotenoid selected from the group consisting of β-carotene, β-cryptoxanthin and zeaxanthin. For example, the β-cryptoxanthin-producing bacteria of the present invention are cultured as described above, and the resulting culture solution may be used directly as β-cryptoxanthin or carotenoids including β-cryptoxanthin. Alternatively, the culture solution is prepared into, for example, a culture supernatant, a microbial cell concentrate (a microbial cell-concentrated solution), wet microbial cells, dried microbial cells, a microbial cell lysate, etc., and these prepared products may be used. Further, carotenoids such as β-cryptoxanthin may be collected from these culture solution or prepared products by extraction, purification or other techniques.

A culture supernatant may be prepared from the culture solution by centrifugation or filtration to remove microbial cells from the culture solution. A microbial cell concentrate (a microbial cell-concentrated solution) may be obtained from the culture solution upon centrifugation, concentration by membrane filtration, or decantation. Wet microbial cells may be obtained from the culture solution by centrifugation or filtration. Dried microbial cells may be obtained from the culture solution, wet microbial cells or microbial cell concentrate (a microbial cell-concentrated solution) upon drying in a standard manner.

In the step of obtaining a microbial cell concentrate, the pH of the culture solution is not limited in any way, but the culture solution may be acidified to facilitate the precipitation of carotenoids. Acidic conditions may be set to any pH within the acidic range, but preferably set to pH 6.5 or less, more preferably pH 5.5 or less, and even more preferably pH 5.0 or less. To enhance the effect of removing unwanted components, the culture solution is also preferably diluted with water and then concentrated. Moreover, water may be added during operation with centrifugation, filtration separation or decantation.

A centrifugal separator for use in centrifugation may be of continuous type or batch type, but preferred for use is a centrifugal separator of continuous type. As to the type of centrifugal separator, examples include those of basket type, multiple-chamber type, decanter type, disc type (nozzle type, desludging type), tubular type and rotor type.

A membrane filtration apparatus for use in filtration separation may be of static type or cross-flow type, but preferred is a membrane filtration apparatus of cross-flow type which is more likely to prevent clogging. The membrane material may be exemplified by filter paper, filter cloth, chemical fiber, ceramic, etc.

Drying may be accomplished in any manner, for example, by spray drying, fluidized drying, fluidized spray drying granulation, drum drying, freeze-drying, etc. After drying, dried microbial cells are also preferably pulverized to give a fine powder. Pulverization may be accomplished in any manner, for example, by beater milling, hammer milling, ball milling, bead milling, etc.

The thus obtained carotenoids such as β-cryptoxanthin or the thus obtained prepared products such as a dried microbial cell composition containing carotenoids including β-cryptoxanthin may be used directly, for example, as feed or food additives.

Moreover, in the present invention, carotenoids such as β-cryptoxanthin or carotenoids may be collected in any manner from the above culture solution or prepared products, and any technique may be used for this purpose as long as it allows the stable and efficient collection of carotenoids. Such a technique may be selected as appropriate by those skilled in the art from among known extraction and purification techniques.

The resulting extracts, prepared products, purified products and so on may be used as carotenoids such as β-cryptoxanthin or carotenoids, either alone or in admixture at any ratio.

EXAMPLES

The present invention will be further described in more detail by way of the following examples, although the present invention is not limited only to these examples.

1. Preparation of Strains

*Paracoccus carotinifaciens* strain E-396 (FERM BP-4283) was subjected to mutagenesis with N-methyl-N'-nitro-N-nitrosoguanidine to select intensely red colonies. The selected strains were cultured in test tubes and measured for carotenoid concentration to select a mutant strain LP-26 with high astaxanthin-producing ability. Then, the strain LP-26 was subjected to mutagenesis with N-methyl-N'-nitro-N-nitrosoguanidine to select yellow to orange colonies, thereby obtaining strains BC-60, BC-65, BCA-26, ZXA-3 and ZXA-23. At least one desired yellow to orange colony was able to be obtained per mutagenesis of the strain LP-26.

When cultured without adjusting the concentration of dissolved oxygen to 0.8 ppm or less, the obtained five strains were all found to produce β-cryptoxanthin, β-carotene and zeaxanthin (“3”). Moreover, 185 strains obtained in the same manner were also confirmed to produce β-cryptoxanthin, β-carotene and zeaxanthin when cultured in 5 L culture tanks (12 strains) or in test tubes (185 strains) without adjusting the concentration of dissolved oxygen to 0.8 ppm or less.

TABLE 3

Amounts of carotenoids produced by 12 strains cultured in 5 L culture tanks

| Strain | β-Carotene per culture solution [mg/L] | Zeaxanthin per culture solution [mg/L] | Total carotenoids per culture solution [mg/L] | β-Cryptoxanthin per culture solution [mg/L] |
|---|---|---|---|---|
| ZXA-13 | 32 | 492 | 532 | 8 |
| ZXA-14 | 21 | 452 | 480 | 7 |
| ZXA-17 | 50 | 675 | 738 | 13 |
| BCA-12 | 7 | 295 | 310 | 8 |
| BCA-22 | 53 | 578 | 645 | 14 |
| BCA-28 | 25 | 580 | 618 | 13 |
| BCA-29 | 6 | 444 | 454 | 4 |
| BCA-30 | 10 | 322 | 341 | 9 |
| BCA-22 | 55 | 583 | 651 | 13 |
| BC-40 | 8 | 278 | 294 | 8 |
| BC-142 | 29 | 379 | 423 | 15 |
| BC-158 | 22 | 201 | 236 | 13 |

2. Culture of Strains

The strains obtained in “1” above were cultured as shown below.

(Seed Culture)

The composition of the medium used for seed culture is as follows: sucrose 30 g/L, corn steep liquor 15 g/L, potassium dihydrogen phosphate 0.54 g/L, dipotassium hydrogen phosphate 2.8 g/L, calcium chloride dihydrate 0.3 g/L, magnesium sulfate heptahydrate 14.3 g/L, iron sulfate heptahydrate 0.3 g/L, defoaming agent 0.1 g/L, pH 7.2.

The medium of the above composition was introduced in 2 L volumes into 5 L culture tanks (jar fermenters) and sterilized by steam at 121° C. for 30 minutes to prepare a seed medium. The strains obtained in “1.” were inoculated into the seed medium and cultured at 28° C. for 30 hours under stirring at 400 rpm. At this stage, the dissolved oxygen concentration was 4.8 ppm. During seed culture, the turbidity was increase by 20.

(Main Culture)

Then, 216 ml of each culture solution after seed culture was inoculated into a 5 L aeration spinner culture tank (jar fermenter) containing 1.8 L of a pigment production medium, followed by culture at 28° C. After 10 to 36 hours (first culture step) had passed from the beginning of main culture, the concentration of dissolved oxygen was controlled to give 0.8 ppm or less dissolved oxygen in the culture solution, and culture was maintained under 0.8 ppm or less dissolved oxygen for 40 to 60 hours (second culture step). The increment of turbidity from the beginning of the first culture step until the completion of the first culture step (measured at a measurement wavelength of 610 nm) was 20 to 400. The concentration of dissolved oxygen was adjusted as follows: a dissolved oxygen electrode was interlocked with the motor of an impeller to automatically adjust the rotational speed of the impeller in response to the value of the dissolved oxygen concentration. Moreover, the lowest rotational speed of the impeller was set to 455 rpm. The pH during culture was controlled to be within the range of 7.0 to 7.4 by continuous dropwise addition of 14% aqueous ammonia. Since glucose is consumed with bacterial growth, glucose was added to maintain a glucose concentration of 5 to 30 g/L in the culture solution. For measurement of β-cryptoxanthin, an aliquot was sampled from the culture solution maintained under 0.8 ppm or less for 40 to 60 hours.

The composition of the pigment production medium is shown below: glucose 40 g/L, potassium dihydrogen phosphate 2.3 g/L, dipotassium hydrogen phosphate 5.7 g/L, ammonium sulfate 2.3 g/L, sodium L-glutamate monohydrate 6 g/L, calcium chloride dihydrate 1.0 g/L, sodium chloride 3 g/L, magnesium sulfate heptahydrate 4.5 g/L, iron sulfate heptahydrate 1.0 g/L, manganese sulfate pentahydrate 0.1 mg/L, boric acid 5 mg/L, zinc sulfate heptahydrate 1.4 mg/L, sodium molybdate dihydrate 2.3 mg/L, copper sulfate pentahydrate 0.63 mg/L, potassium iodide 1.0 mg/L, cobalt chloride hexahydrate 0.10 mg/L, sodium tungstate 1 mg/L, nickel sulfate hexahydrate 1 mg/L, sodium selenate 0.1 mg/L, aluminum (III) chloride hexahydrate 0.1 mg/L, chromium (III) chloride hexahydrate 0.1 mg/L, myo-inositol 50 mg/L, ascorbic acid 30 mg/L, pyridoxine hydrochloride 20 mg/L, calcium pantothenate 15 mg/L, riboflavin 10 mg/L, p-aminobenzoic acid 10 mg/L, choline 10 mg/L, cyanocobalamin 5 mg/L, thiamine hydrochloride 30 mg/L, folic acid 1 mg/L, niacin 15 mg/L, biotin 0.050 mg/L, polyether-based defoaming agent 0.5 g/L.

[Measurement Procedures]

For measurement of dissolved oxygen, the following apparatus was used.

DO measurement apparatus: a product of B. E. Marubishi Co., Ltd., Japan, model number OX-2500

The turbidity of the culture solution was measured as follows. The turbidity of the culture solution is measured with a universal spectrophotometer. The turbidity may be measured, for example, with an Erma spectrophotometer (model number: AE-450). The turbidity is calculated from the absorbance measured using a quartz cuvette with an optical path length of 1 cm at a measurement wavelength of 610 nm. The turbidity is corrected assuming that the value measured for water is set to 0. The absorbance takes a value between 0 and 1 inclusive, but a value too close to 1 may not be measured accurately, so that the culture solution is optionally diluted with water before measurement in an attempt to give a measured value of 0.7 or less. To calculate the turbidity of the diluted culture solution, the absorbance obtained from measurement is corrected by being multiplied by a dilution factor.

3. Measurement of β-Cryptoxanthin

The amounts of β-cryptoxanthin, zeaxanthin and β-carotene were measured by using HPLC (Waters Alliance system (separation module e2695, detector 2489)).

Two columns of Inertsil SIL-100A, 5 μm (ϕ4.6 mm×250 mm) (GL Sciences Inc., Japan) were connected together for use as a column. For elution, a mixed solution of n-hexane, tetrahydrofuran and methanol (20:40:1) serving as a mobile phase was passed through the column at a flow rate of 1.0 mL per minute at a constant temperature around room temperature.

The culture solutions sampled in "2." above were each dissolved in a mixed solution of n-hexane, tetrahydrofuran and methanol (40:20:1), and the resulting samples were diluted 10-fold with the mobile phase, 20 μL aliquots of which were then injected into the column. The column eluates were detected at a wavelength of 455 nm. Moreover, as standards for quantification, β-cryptoxanthin (EXTRASYNTHESE S.A., Cat. No. 0317S), zeaxanthin (EXTRASYNTHESE S.A., Cat. No. 0307S) and β-carotene (FUJIFILM Wako Pure Chemical Corporation, Japan, Cat. No. 031-05531) were used.

The results obtained are shown below.

TABLE 5

Table 5 Gene analysis results of strains BC-60 and BC-65

SEQ ID NO: 3 (strain BC-60, strain BC-65): comprising a mutation from a tryptophan-encoding codon (ugg) to a stop codon (uga)

ATGAGCGCACATGCCCTGCCCAAGGCAGATCTGACCGCCACCAGTTTGAT
CGTCTCGGGCGGCATCATCGCCGCGTGGCTGGCCCTGCATGTGCATGCGC
TGTGGTTTCTGGACGCGGCGGCGCATCCCATCCTGGCGGTCGCGAATTTC
CTGGGGCTGACCTGGCTGTCGGTCGGTCTGTTCATCATCGCGCATGACGC
GATGCATGGGTCGGTCGTGCCGGGGCGCCCGCGCGCCAATGCGGCGATGG
GCCAGCTTGTCCTGTGGCTGTATGCCGGATTTTCCTGGCGCAAGATGATC
GTCAAGCACATGGCCCATCATCGCCATGCCGGAACCGACGACGACCCAGA
TTTCGACCATGGCGGCCCGGTCCGCTGGTACGCCCGCTTCATCGGCACCT

TABLE 4

| Measurement results | | | | | | | | |
|---|---|---|---|---|---|---|---|---|
| | Strain | Dissolved oxygen concentration (DO) [ppm] | Total carotenoids per culture solution [mg/L] | β-Cryptoxanthin concentration relative to total carotenoids [% by mass] | β-Cryptoxanthin per culture solution [mg/L] | Zeaxanthin per culture solution [mg/L] | β-Carotene per culture solution [mg/L] |
| Example 1 | BC-60 | 0.8 | 283 | 9.4 | 27 | 157 | 100 |
| Example 2 | BC-60 | 0.8 | 288 | 10 | 29 | 154 | 105 |
| Example 3 | BC-65 | 0.8 | 451 | 4.9 | 22 | 399 | 30 |
| Example 4 | BCA-26 | 0.8 | 213 | 14 | 29 | 157 | 27 |
| Example 5 | ZXA-3 | 0.4 | 378 | 6.9 | 26 | 328 | 24 |
| Example 6 | ZXA-23 | 0.4 | 337 | 8.1 | 27 | 285 | 25 |
| Comparative Example 1 | BC-60 | 2.4 | 397 | 3.4 | 13 | 348 | 35 |
| Comparative Example 2 | ZXA-3 | 2.4 | 780 | 2 | 13 | 709 | 58 |
| Comparative Example 3 | BC-65 | 2.4 | 418 | 3.4 | 14 | 377 | 27 |
| Comparative Example 4 | BCA-26 | 2 | 406 | 3 | 12 | 376 | 18 |
| Comparative Example 5 | ZXA-23 | 2.4 | 530 | 1.7 | 9 | 481 | 40 |

The five strains obtained in "1." above (i.e., the strains BC-60, BC-65, BCA-26, ZXA-3 and ZXA-23) were all found to produce β-cryptoxanthin, β-carotene and β-cryptoxanthin. The results shown in Table 4 indicated that the amount of β-carotenoid production was improved when β-carotenoid-producing bacteria were cultured at a dissolved oxygen concentration of 0.8 ppm or less. In particular, the amount of β-cryptoxanthin per culture solution and the β-cryptoxanthin concentration relative to the total amount of carotenoids were significantly improved when compared to culture at a dissolved oxygen concentration greater than 0.8 ppm (Comparative Examples).

Moreover, the carotenoids measured were β-carotene, β-cryptoxanthin and zeaxanthin in all cases, and the production of adonixanthin and astaxanthin was not detected.

4. Gene Analysis of Bacteria

(1) Gene Analysis of Strains BC-60 and BC-65

The strains BC-60 and BC-65 were subjected to gene analysis. As a result, these strains were found to have a mutation in the CrtW gene.

TABLE 5-continued

Table 5 Gene analysis results of strains BC-60 and BC-65

ATTTCGGCTGGCGCGAGGGGCTGCTGCTGCCCGTCATCGTGACGGTCTAT
GCGCTGATGTTGGGGGATCGCTGGATGTACGTGGTCTTCTGGCCGTTGCC
GTCGATCCTGGCGTCGATCCAGCTGTTCGTGTTCGGCACTTGGCTGCCGC
ACCGCCCCGGCCACGACGCGTTCCCGGACCGCCACAATGCGCGGTCGTCG
CGGATCAGCGACCCCGTGTCGCTGCTGACCTGCTTTCACTTTGGCGGTTA
TCATCACGAACACCACCTGCACCCGACGGTGCCTTGGTGACGCCTGCCCA
GCACCCGCACCAAGGGGGACACCGCATGA

SEQ ID NO: 4 (strain BC-60, strain BC-65)

MSAHALPKADLTATSLIVSGGIIAAWLALHVHALWFLDAAAHPILAVANF
LGLTWLSVGLFIIAHDAMHGSVVPGRPRANAAMGQLVLWLYAGFSWRKMI
VKHMAHHRHAGTDDDPDFDHGGPVRWYARFIGTYFGWREGLLLPVIVTVY
ALMLGDRWMYVVFWPLPSILASIQLFVFGTWLPHRPGHDAFPDRHNARSS
RISDPVSLLTCFHFGGYHHEHHLHPTVPW

BC-60 and BC-65 were both found to have a mutation from a tryptophan-encoding codon (ugg) on the CrtW gene to a stop codon (uga: expressed as "TGA" in Table 5, A is indicated in boldface type). Namely, the crtW gene has a stop codon (tryptophan→stop) to thereby discontinue protein synthesis, which indicates that the crtW enzyme does not function normally.

(2) Gene Analysis of Strain ZXA-23

ZXA-23 was subjected to gene analysis. As a result, this strain was found to have a mutation in the CrtW gene, and a codon (cau) encoding histidine at position 65 of the CrtW enzyme amino acid sequence was mutated to a tyrosine-encoding codon (uau: expressed as "TAT" in Table 6, the first T is indicated in boldface type).

TABLE 6

| Table 6 Gene analysis results of strain ZXA-23 |
|---|
| SEQ ID NO: 5 (strain ZXA-23): comprising a mutation from a histidine-encoding codon (cau) to a tyrosine-encoding codon (uau) |
| ATGAGCGCACATGCCCTGCCCAAGGCAGATCTGACCGCCACCAGTTTGAT<br>CGTCTCGGGCGGCATCATCGCCGCGTGGCTGGCCCTGCATGTGCATGCGC<br>TGTGGTTTCTGGACGCGGCGGCGCATCCCATCCTGGCGGTCGCGAATTTC<br>CTGGGGCTGACCTGGCTGTCGGTCGGTCTGTTCATCATCGCGTATGACGC<br>GATGCATGGGTCGGTCGTGCCGGGGCGCCCGCGCGCCAATGCGGCGATGG<br>GCCAGCTTGTCCTGTGGCTGTATGCCGGATTTTCCTGGCGCAAGATGATC<br>GTCAAGCACATGGCCCATCATCGCCATGCCGGAACCGACGACGACCCAGA<br>TTTCGACCATGGCGGCCCGGTCCGCTGGTACGCCCGCTTCATCGGCACCT<br>ATTTCGGCTGGCGCGAGGGGCTGCTGCTGCCCGTCATCGTGACGGTCTAT<br>GCGCTGATGTTGGGGGATCGCTGGATGTACGTGGTCTTCTGGCCGTTGCC<br>GTCGATCCTGGCGTCGATCCAGCTGTTCGTGTTCGGCACTTGGCTGCCGC<br>ACCGCCCCGGCCACGACGCGTTCCCGGACCGCCACAATGCGCGGTCGTCG<br>CGGATCAGCGACCCCGTGTCGCTGCTGACCTGCTTTCACTTTGGCGGTTA<br>TCATCACGAACACCACCTGCACCCGACGGTGCCTTGGTGGCGCCTGCCCA<br>GCACCCGCACCAAGGGGGACACCGCATGA |
| SEQ ID NO: 6 (strain ZXA-23): comprising a mutation from histidine to tyrosine in the amino acid at position 65 |
| MSAHALPKADLTATSLIVSGGIIAAWLALHVHALWFLDAAAHPILAVANF<br>LGLTWLSVGLFIIAYDAMHGSVVPGRPRANAAMGQLVLWLYAGFSWRKMI<br>VKHMAHHRHAGTDDDPDFDHGGPVRWYARFIGTYFGWREGLLLPVIVTVY<br>ALMLGDRWMYVVFWPLPSILASIQLFVFGTWLPHRPGHDAFPDRHNARSS<br>RISDPVSLLTCFHFGGYHHEHHLHPTVPWWRLPSTRTKGDTA |

(3) Gene analysis of Strain ZXA-3

ZXA-3 was subjected to gene analysis. As a result, this strain was found to have a mutation in the CrtW gene, and a codon (cau) encoding histidine at position 65 of the CrtW enzyme amino acid sequence was mutated to a tyrosine-encoding codon (uau: expressed as "TAT" in Table 6, the first T is indicated in boldface type) (SEQ ID NO: 5 and SEQ ID NO: 6). The mutation in the strain ZXA-3 was the same as the mutation in the strain ZXA-23.

Histidine at position 65 of the CrtW enzyme amino acid sequence has been shown to be important for CrtW enzyme activity (Rick et al., Appl Environ Microbiol. 2006 September; 72(9):5829-37). In the mutated CrtW enzyme, a positively charged basic amino acid, histidine, has been mutated to a non-charged neutral amino acid, tyrosine; and hence it is inferred that the enzyme activity will be significantly impaired.

The foregoing results prove that in these mutant strains, their endogenous crtW gene has been partially or completely deleted or inactivated to thereby lose the ability to produce a functional crtW enzyme (β-carotene ketolase).

Moreover, if the crtW enzyme functions in bacteria, adonixanthin is produced because β-carotene and zeaxanthin are converted into adonixanthin by the action of the crtW enzyme. Adonixanthin produced by bacteria is detected by HPLC. On the other hand, in the strains of the present invention, adonixanthin is not detected by HPLC. Thus, the strains of the present invention are deemed to lose the ability to produce functional β-carotene ketolase because their endogenous crtW gene has been partially or completely deleted or inactivated.

INDUSTRIAL APPLICABILITY

The present invention enables the provision of bacteria producing at least one carotenoid selected from the group consisting of β-carotene, β-cryptoxanthin and zeaxanthin. The present invention enables an improvement in the amount of β-cryptoxanthin production when bacteria producing at least one carotenoid selected from the group consisting of β-carotene, β-cryptoxanthin and zeaxanthin are cultured at a given dissolved oxygen concentration.

The invention claimed is:

1. A method for β-cryptoxanthin, said method comprising:

culturing bacteria from the genus *Paracoccus*, thereby obtaining β-cryptoxanthin, wherein, during the culturing, the concentration of dissolved oxygen in a culture solution is 0.8 ppm or less, as measured with a dissolved oxygen electrode, wherein the bacteria of the genus *Paracoccus* are bacteria forming yellow to orange colonies; or bacteria whose endogenous crtW gene has been partially or completely deleted or inactivated to lose the ability to produce a functional crtW enzyme, and wherein the amount of β-cryptoxanthin production obtained after completion of the culture is 15 mg/L or more per culture solution.

2. A method for producing β-cryptoxanthin, said method comprising:

(a) first culturing of bacteria from the genus *Paracoccus* where the bacteria of the genus *Paracoccus* are allowed to grow in a culture solution, or where the bacteria of the genus *Paracoccus* are cultured until the turbidity of the culture solution measured at a measurement wavelength of 610 nm is increased by 5 or more compared to the turbidity at the beginning of the first culturing; and (b) second culturing of bacteria from the genus *Paracoccus* where after completion of the first culture step, wherein, during the second culturing, the bacteria of the genus *Paracoccus* are cultured in a culture solution whose dissolved oxygen concentration is 0.8 ppm or less, thereby obtaining β-cryptoxanthin, wherein the dissolved oxygen concentration of the culture solution is measured with a dissolved oxygen electrode, wherein the bacteria of the genus *Paracoccus* are bacteria forming yellow to orange colonies; or bacteria whose endogenous crtW gene has been partially or completely deleted or inactivated to lose the ability to produce a functional crtW enzyme, and wherein the amount of β-cryptoxanthin production obtained after completion of the second culturing is 15 mg/L or more per culture solution.

3. The method according to claim 2, wherein the culture period in the second culturing is 10 hours or more and 100 hours or less.

4. The method according to claim 2, wherein the culture period in the first culturing is 10 hours or more and 70 hours or less.

5. The method according to claim 1, wherein the bacteria forming yellow to orange colonies are obtained by selecting yellow to orange colonies generated upon mutagenesis of bacteria of the genus *Paracoccus* that form red colonies.

6. The method according to claim 1, wherein the endogenous crtW gene comprises a nucleotide sequence at least 90% identical to the nucleotide sequence shown in SEQ ID NO: 1.

7. The method according to claim 1, wherein the crtW enzyme comprises an amino acid sequence at least 90% identical to the amino acid sequence shown in SEQ ID NO: 2.

8. The method according to claim 1, wherein the concentration of dissolved oxygen in the culture solution is adjusted to 0.4 ppm or less.

9. The method according to claim 2, wherein the concentration of dissolved oxygen in the culture solution is adjusted to 0.4 ppm or less.

* * * * *

SEQUENCE LISTING

<160> NUMBER OF SEQ ID NOS: 7

<210> SEQ ID NO 1
<211> LENGTH: 729
<212> TYPE: DNA
<213> ORGANISM: Paracoccus carotinifaciens

<400> SEQUENCE: 1
atgagcgcac atgccctgcc caaggcagat ctgaccgcca ccagtttgat cgtctcgggc 60
ggcatcatcg ccgcgtggct ggccctgcat gtgcatgcgc tgtggtttct ggacgcggcg 120
gcgcatccca tcctggcggt cgcgaatttc ctggggctga cctggctgtc ggtcggtctg 180
ttcatcatcg cgcatgacgc gatgcatggg tcggtcgtgc cggggcgccc gcgcgccaat 240
gcggcgatgg gccagcttgt cctgtggctg tatgccggat tttcctggcg caagatgatc 300
gtcaagcaca tggcccatca tcgccatgcc ggaaccgacg acgacccaga tttcgaccat 360
ggcggcccgg tccgctggta cgcccgcttc atcggcacct atttcggctg gcgcgagggg 420
ctgctgctgc ccgtcatcgt gacggtctat gcgctgatgt tgggggatcg ctggatgtac 480
gtggtcttct ggccgttgcc gtcgatcctg gcgtcgatcc agctgttcgt gttcggcact 540
tggctgccgc accgccccgg ccacgacgcg ttcccggacc gccacaatgc gcggtcgtcg 600
cggatcagcg accccgtgtc gctgctgacc tgctttcact ttggcggtta tcatcacgaa 660
caccacctgc acccgacggt gccttggtgg cgcctgccca gcacccgcac caagggggac 720
accgcatga 729

<210> SEQ ID NO 2
<211> LENGTH: 242
<212> TYPE: PRT
<213> ORGANISM: Paracoccus carotinifaciens

<400> SEQUENCE: 2

Met Ser Ala His Ala Leu Pro Lys Ala Asp Leu Thr Ala Thr Ser Leu
1 5 10 15

Ile Val Ser Gly Gly Ile Ile Ala Ala Trp Leu Ala Leu His Val His
20 25 30

Ala Leu Trp Phe Leu Asp Ala Ala Ala His Pro Ile Leu Ala Val Ala
35 40 45

Asn Phe Leu Gly Leu Thr Trp Leu Ser Val Gly Leu Phe Ile Ile Ala
50 55 60

His Asp Ala Met His Gly Ser Val Val Pro Gly Arg Pro Arg Ala Asn
65 70 75 80

Ala Ala Met Gly Gln Leu Val Leu Trp Leu Tyr Ala Gly Phe Ser Trp
85 90 95

Arg Lys Met Ile Val Lys His Met Ala His His Arg His Ala Gly Thr
100 105 110

Asp Asp Asp Pro Asp Phe Asp His Gly Gly Pro Val Arg Trp Tyr Ala
115 120 125

Arg Phe Ile Gly Thr Tyr Phe Gly Trp Arg Glu Gly Leu Leu Leu Pro
130 135 140

Val Ile Val Thr Val Tyr Ala Leu Met Leu Gly Asp Arg Trp Met Tyr
145 150 155 160

Val Val Phe Trp Pro Leu Pro Ser Ile Leu Ala Ser Ile Gln Leu Phe
165 170 175

Val Phe Gly Thr Trp Leu Pro His Arg Pro Gly His Asp Ala Phe Pro
180 185 190

Asp Arg His Asn Ala Arg Ser Ser Arg Ile Ser Asp Pro Val Ser Leu
195 200 205

Leu Thr Cys Phe His Phe Gly Gly Tyr His His Glu His His Leu His
210 215 220

Pro Thr Val Pro Trp Trp Arg Leu Pro Ser Thr Arg Thr Lys Gly Asp
225 230 235 240

Thr Ala

<210> SEQ ID NO 3
<211> LENGTH: 729
<212> TYPE: DNA
<213> ORGANISM: Paracoccus carotinifaciens

<400> SEQUENCE: 3
atgagcgcac atgccctgcc caaggcagat ctgaccgcca ccagtttgat cgtctcgggc 60
ggcatcatcg ccgcgtggct ggccctgcat gtgcatgcgc tgtggtttct ggacgcggcg 120
gcgcatccca tcctggcggt cgcgaatttc ctggggctga cctggctgtc ggtcggtctg 180
ttcatcatcg cgcatgacgc gatgcatggg tcggtcgtgc cggggcgccc gcgcgccaat 240

```
gcggcgatgg gccagcttgt cctgtggctg tatgccggat tttcctggcg caagatgatc    300

gtcaagcaca tggcccatca tcgccatgcc ggaaccgacg acgacccaga tttcgaccat    360

ggcggcccgg tccgctggta cgcccgcttc atcggcacct atttcggctg gcgcgagggg    420

ctgctgctgc ccgtcatcgt gacggtctat gcgctgatgt tgggggatcg ctggatgtac    480

gtggtcttct ggccgttgcc gtcgatcctg gcgtcgatcc agctgttcgt gttcggcact    540

tggctgccgc accgccccgg ccacgacgcg ttcccggacc gccacaatgc gcggtcgtcg    600

cggatcagcg accccgtgtc gctgctgacc tgctttcact ttggcggtta tcatcacgaa    660

caccacctgc acccgacggt gccttggtga cgcctgccca gcacccgcac caagggggac    720

accgcatga                                                            729
```

```
<210> SEQ ID NO 4
<211> LENGTH: 229
<212> TYPE: PRT
<213> ORGANISM: Paracoccus carotinifaciens

<400> SEQUENCE: 4

Met Ser Ala His Ala Leu Pro Lys Ala Asp Leu Thr Ala Thr Ser Leu
1               5                   10                  15

Ile Val Ser Gly Gly Ile Ile Ala Ala Trp Leu Ala Leu His Val His
            20                  25                  30

Ala Leu Trp Phe Leu Asp Ala Ala Ala His Pro Ile Leu Ala Val Ala
        35                  40                  45

Asn Phe Leu Gly Leu Thr Trp Leu Ser Val Gly Leu Phe Ile Ile Ala
    50                  55                  60

His Asp Ala Met His Gly Ser Val Val Pro Gly Arg Pro Arg Ala Asn
65                  70                  75                  80

Ala Ala Met Gly Gln Leu Val Leu Trp Leu Tyr Ala Gly Phe Ser Trp
                85                  90                  95

Arg Lys Met Ile Val Lys His Met Ala His His Arg His Ala Gly Thr
            100                 105                 110

Asp Asp Asp Pro Asp Phe Asp His Gly Gly Pro Val Arg Trp Tyr Ala
        115                 120                 125

Arg Phe Ile Gly Thr Tyr Phe Gly Trp Arg Glu Gly Leu Leu Leu Pro
    130                 135                 140

Val Ile Val Thr Val Tyr Ala Leu Met Leu Gly Asp Arg Trp Met Tyr
145                 150                 155                 160

Val Val Phe Trp Pro Leu Pro Ser Ile Leu Ala Ser Ile Gln Leu Phe
                165                 170                 175

Val Phe Gly Thr Trp Leu Pro His Arg Pro Gly His Asp Ala Phe Pro
            180                 185                 190

Asp Arg His Asn Ala Arg Ser Ser Arg Ile Ser Asp Pro Val Ser Leu
        195                 200                 205

Leu Thr Cys Phe His Phe Gly Gly Tyr His His Glu His His Leu His
    210                 215                 220

Pro Thr Val Pro Trp
225
```

```
<210> SEQ ID NO 5
<211> LENGTH: 729
<212> TYPE: DNA
<213> ORGANISM: Paracoccus carotinifaciens

<400> SEQUENCE: 5
```

```
atgagcgcac atgccctgcc caaggcagat ctgaccgcca ccagtttgat cgtctcgggc     60

ggcatcatcg ccgcgtggct ggccctgcat gtgcatgcgc tgtggtttct ggacgcggcg    120

gcgcatccca tcctggcggt cgcgaatttc ctggggctga cctggctgtc ggtcggtctg    180

ttcatcatcg cgtatgacgc gatgcatggg tcggtcgtgc cggggcgccc gcgcgccaat    240

gcggcgatgg gccagcttgt cctgtggctg tatgccggat ttcctggcg caagatgatc     300

gtcaagcaca tggcccatca tcgccatgcc ggaaccgacg acgacccaga tttcgaccat    360

ggcggcccgg tccgctggta cgcccgcttc atcggcacct atttcggctg gcgcgagggg    420

ctgctgctgc ccgtcatcgt gacggtctat gcgctgatgt tgggggatcg ctggatgtac    480

gtggtcttct ggccgttgcc gtcgatcctg gcgtcgatcc agctgttcgt gttcggcact    540

tggctgccgc accgccccgg ccacgacgcg ttcccggacc gccacaatgc gcggtcgtcg    600

cggatcagcg accccgtgtc gctgctgacc tgctttcact ttggcggtta tcatcacgaa    660

caccacctgc acccgacggt gccttggtgg cgcctgccca gcacccgcac caagggggac    720

accgcatga                                                            729
```

```
<210> SEQ ID NO 6
<211> LENGTH: 242
<212> TYPE: PRT
<213> ORGANISM: Paracoccus carotinifaciens

<400> SEQUENCE: 6

Met Ser Ala His Ala Leu Pro Lys Ala Asp Leu Thr Ala Thr Ser Leu
1               5                   10                  15

Ile Val Ser Gly Gly Ile Ile Ala Ala Trp Leu Ala Leu His Val His
            20                  25                  30

Ala Leu Trp Phe Leu Asp Ala Ala Ala His Pro Ile Leu Ala Val Ala
        35                  40                  45

Asn Phe Leu Gly Leu Thr Trp Leu Ser Val Gly Leu Phe Ile Ile Ala
    50                  55                  60

Tyr Asp Ala Met His Gly Ser Val Val Pro Gly Arg Pro Arg Ala Asn
65                  70                  75                  80

Ala Ala Met Gly Gln Leu Val Leu Trp Leu Tyr Ala Gly Phe Ser Trp
                85                  90                  95

Arg Lys Met Ile Val Lys His Met Ala His His Arg His Ala Gly Thr
            100                 105                 110

Asp Asp Asp Pro Asp Phe Asp His Gly Gly Pro Val Arg Trp Tyr Ala
        115                 120                 125

Arg Phe Ile Gly Thr Tyr Phe Gly Trp Arg Glu Gly Leu Leu Leu Pro
    130                 135                 140

Val Ile Val Thr Val Tyr Ala Leu Met Leu Gly Asp Arg Trp Met Tyr
145                 150                 155                 160

Val Val Phe Trp Pro Leu Pro Ser Ile Leu Ala Ser Ile Gln Leu Phe
                165                 170                 175

Val Phe Gly Thr Trp Leu Pro His Arg Pro Gly His Asp Ala Phe Pro
            180                 185                 190

Asp Arg His Asn Ala Arg Ser Ser Arg Ile Ser Asp Pro Val Ser Leu
        195                 200                 205

Leu Thr Cys Phe His Phe Gly Gly Tyr His His Glu His His Leu His
    210                 215                 220

Pro Thr Val Pro Trp Trp Arg Leu Pro Ser Thr Arg Thr Lys Gly Asp
225                 230                 235                 240
```

-continued

```
Thr Ala


<210> SEQ ID NO 7
<211> LENGTH: 1452
<212> TYPE: DNA
<213> ORGANISM: Paracoccus carotinifaciens
<220> FEATURE:
<221> NAME/KEY: misc_feature
<222> LOCATION: (1350)..(1350)
<223> OTHER INFORMATION: n is a, c, g, or t

<400> SEQUENCE: 7

agtttgatcc tggctcagaa cgaacgctgg cggcaggctt aacacatgca agtcgagcga      60

gaccttcggg tctagcggcg gacgggtgag taacgcgtgg gaacgtgccc ttctctacgg     120

aatagccccg ggaaactggg agtaataccg tatacgccct ttgggggaaa gatttatcgg     180

agaaggatcg gcccgcgttg gattaggtag ttggtggggt aatggcccac caagccgacg     240

atccatagct ggtttgagag gatgatcagc cacactggga ctgagacacg gcccagactc     300

ctacgggagg cagcagtggg gaatcttaga caatgggggc aaccctgatc tagccatgcc     360

gcgtgagtga tgaaggcctt agggttgtaa agctctttca gctgggaaga taatgacggt     420

accagcagaa gaagccccgg ctaactccgt gccagcagcc gcggtaatac ggagggggct     480

agcgttgttc ggaattactg ggcgtaaagc gcacgtaggc ggactggaaa gtcagaggtg     540

aaatcccagg gctcaacctt ggaactgcct ttgaaactat cagtctggag ttcgagagag     600

gtgagtggaa ttccgagtgt agaggtgaaa ttcgtagata ttcggaggaa caccagtggc     660

gaaggcggct cactggctcg atactgacgc tgaggtgcga aagcgtgggg agcaaacagg     720

attagatacc ctggtagtcc acgccgtaaa cgatgaatgc cagacgtcgg caagcatgct     780

tgtcggtgtc acacctaacg gattaagcat tccgcctggg gagtacggtc gcaagattaa     840

aactcaaagg aattgacggg ggcccgcaca agcggtggag catgtggttt aattcgaagc     900

aacgcgcaga accttaccaa cccttgacat ggcaggaccg ctggagagat tcagctttct     960

cgtaagagac ctgcacacag gtgctgcatg gctgtcgtca gctcgtgtcg tgagatgttc    1020

ggttaagtcc ggcaacgagc gcaacccacg tccctagttg ccagcaattc agttgggaac    1080

tctatggaaa ctgccgatga taagtcggag gaaggtgtgg atgacgtcaa gtcctcatgg    1140

gccttacggg ttgggctaca cacgtgctac aatggtggtg acagtgggtt aatccccaaa    1200

agccatctca gttcggattg tcctctgcaa ctcgagggca tgaagttgga atcgctagta    1260

atcgcggaac agcatgccgc ggtgaatacg ttcccgggcc ttgtacacac cgcccgtcac    1320

accatgggag ttggttctac ccgacgacgn tgcgctaacc ttcgggggc aggcggccac    1380

ggtaggatca gcgactgggg tgaagtcgta acaaggtagc cgtaggggaa cctgcggctg    1440

gatcacctcc tt                                                        1452
```